United States Patent [19]

Wunsch et al.

[11] 3,978,035

[45] Aug. 31, 1976

[54] 13-NORLEUCINE-14-DESAMIDO MOTILIN, A METHOD FOR PREPARING IT AND AN AGENT CONTAINING IT

[75] Inventors: Erich Wunsch, Tutzing; Gerhard Wendlberger, Taufkirchen; Ernst Jaeger, Germering; Regine Scharf, Munich; Karl-Heinz Deimer, Germering; Hans Stocker, Prien, all of Germany

[73] Assignee: Max-Planck-Gesellschaft zur Forderung der Wissenschaften e.V., Gottingen, Germany

[22] Filed: Mar. 27, 1974

[21] Appl. No.: 455,396

[30] Foreign Application Priority Data

Mar. 27, 1973 Germany............................ 2315271

[52] U.S. Cl.......................... 260/112.5 R; 424/177
[51] Int. Cl.².................. C07C 103/52; A61K 37/00
[58] Field of Search.................. 260/112.5; 424/177

[56] References Cited
OTHER PUBLICATIONS
Brown et al., Can. J. Biochem., 51, 533–537 (1973).

Brown et al., Chem. Abstr. 76:150240m (1972).

*Primary Examiner*—Lewis Gotts
*Assistant Examiner*—Reginald J. Suyat
*Attorney, Agent, or Firm*—Christen & Sabol

[57] ABSTRACT

The specification describes the total synthesis of L-norleucine-13-motilin based on the replacement of the L-methionine radical located in the 13-position by an L-norleucine radical. In accordance with the present day development of peptide synthesis the central arginyl-methionyl-bond (amino acids 12 and 13 of motilin) can in practice hardly be synthesised, while on the other hand the norleucine-13-docosapeptide corresponding to motilin can be more readily produced synthetically, and this provides for a comparatively rapid determination of structure and can give important information as regards the biological effect specificity of methionine.

7 Claims, 7 Drawing Figures

13-NORLEUCINE-14-DESAMIDO MOTILIN, A METHOD FOR PREPARING IT AND AN AGENT CONTAINING IT

The invention relates more especially to 13-norleucine-14-desamido-motilin, which differs from naturally occurring motilin in that in the polypeptide chain made up of 22 amino acids in all the 13th amino acid, an L-methionine radical of the formula

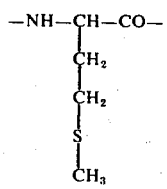

is replaced by an L-norleucine radical of the formula

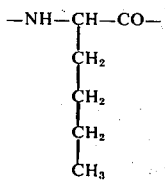

As is known motilin is a polypeptide which stimulates the motor activity both in the antrum and also in the fundus gland areas of the stomach, and as such has been isolated from the duodenal mucous membrane of the small intestine of the pig (see in this connection for example "Can. J. Physiol. Pharmacol.", vol. 49, 1971, pages 399 to 405, and "Gastroenterology", vol. 62, 1972, pages 401 to 404), and stimulates pepsin release without a change in $H^+$ secretion and differs both chemically and also physiologically from gastrointestinal hormones which in the meantime have been explained.

Motilin is therefore of substantial importance both as a therapeutic agent and also for diagnosis. As is the case with every naturally occurring substance there is the problem that the isolation from animal organs for example is extremely time-consuming and expensive and can only be caried out with minimum yields.

One aim of the invention is that of indicating means and routes which offer the possibility of synthetically producing and using a compound with a motiline action even on a large scale.

The invention is based on the discovery that the aim indicated can be achieved by carrying out a total synthesis of motilin with the replacement of the L-methionine radical located in the 13-position by an L-norleucine radical owing to the consideration that in accordance with the present day development of peptide synthesis the central arginyl-methionyl-bond (amino acids 12 to 13 of motiline) can in practice hardly be synthesised, while on the other hand the norleucine-13-docosapeptide corresponding to motilin can be more readily produced synthetically, and provides for a comparatively rapid determination of sturcture and can give important information as regards the biological effect specificity of methionine.

The subject matter of the invention is 13-norleucine-14-desamido motilin of the formula H-Phe-Val-Pro-Ile-Phe-Thr-Tyr-Gly-Glu-Leu-Gln
 (1) (2) (3) (4) (5) (6) (7) (8) (9) (10) (11)
Arg-Nle-Glu-Glu-Lys-Glu-Arg-Asn-Lys-Gly-Gln-OH
 (12) (13) (14) (15) (16) (17) (18) (19) (20) (21) (22)

in which the numbers given in brackets denote the amino acid radicals serially numbered, all amino acids being in the L-configuration apart from glycine. In that formula: Phe denotes the phenylalanine radical (amino acids 1 and 5) of the formula

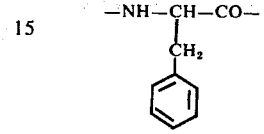

Val denotes the valine radical (amino acid 2) of the formula

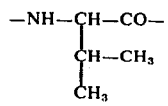

Pro the proline radical (amino acid 3) of the formula

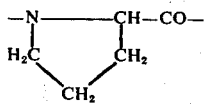

Ile the isoleucine radical (amino acid 4) of the formula

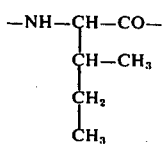

Thr the threonine radical (amino acid 6) of the formula

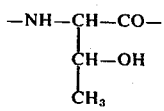

Tyr the tyrosine radical (amino acid 7) of the formula

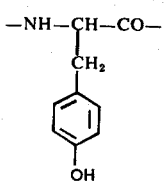

Gly the glycine radical (amino acids 8 and 21) of the formula

Glu the glutamic acid radical (amino acids 9, 14, 15 and 17) of the formula

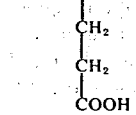

Leu the leucine radical (amino acid 10) of the formula

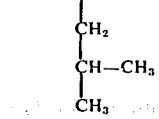

Gln the glutamine radical (amino acids 11 and 22) of the formula

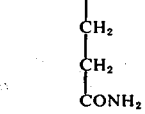

Arg the arginine radical (amino acids 12 and 18) of the formula

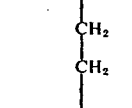

Nle the norleucine radical (amino acid 13) of the formula

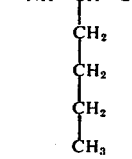

Lys the lysine radical (amino acids 16 and 20) of the formula

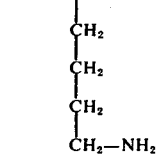

and Asn the asparagine radical (amino acid 19) of the formula

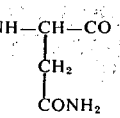

The subject matter of the invention also comprises a method for the production of 13-norleucine-14-desamido motilin which is characterized in that a. the sequence parts capable of being joined fragment I consisting of arginyl-(hydrobromide)-asparaginyl-Nε-tert.butyloxycarbonyl-lysyl-glycyl-glutamine-tert.butyl ester (amino acids 18–22)

fragment II consisting of Nα-benzyloxycarbonyl-glutamyl-(γ-tert.butyl ester)-glutamyl-(γ-tert.butyl ester)-Nε-tert.butyloxycarbonyl-lysyl-glutamic acid-(γ-tert.butyl ester) (amino acids 14 to 17), fragment III consisting of Nα-benzyloxycarbonyl-Nδ, Nω-di-benzyloxycarbonyl-arginyl-norleucine (amino acids 12 and 13), fragment IV consisting of Nα-benzyloxycarbonyl-glutamyl-(γ-tert.butyl ester)-leucyl-glutamine (amino acids 9–11), fragment V consisting O-tert.butyl-threonyl-O-tert.butyl-tyrosyl-glycine O-tert.-butyl-threonyl-O-tert.butyl-tyrosyl-glycine (amino acids 6–8), and fragment VI consisting of Nα-tert.butyloxycarbonyl-phenyl-alanyl-valyl-prolyl-isoleucyl-phenlalanine (amino acids 1–5) are formed, in which all side chain functions of the polyfunctional amino acids carry protective groups on a tert.alcohol basis and which can acidolytically easily be split off and the complex function of the arginine is masked partially by Nδ, ω-diacylation and partly by a protonisation brought about by salt formation with hydrogen bromide b. the fragments I to VI are connected together with help of the known N,N'-dicyclohexylcarbodiimide-N-hydroxysuccinimide method (preferred) or by a modification of this method found in the literature, c. from the so obtained polypeptide masked on all sides and having the overall sequence of the amino acids 1 – 22 all protective groups are split off with the help of trifluoroacetic acid and following this the trifluoroacetate and bromide ions are removed with the help of an anion exchange resin, and d. the 13-norleucine-14-desamido-motilin obtained is isolated and purified.

A first subembodiment of the method is characterized in that the fragment I is produced by esterifying Nα-benzyloxycarbonyl-glutamine with acetic acid tert.butyl ester with sulfuric acid catalysis and following hydrogenolytic removal of the N-protective group to form glutamine tert.butyl ester (amino acid 22), the ester obtained is linked with Nα-benzyl-oxycarbonyl-glycine-N-hydroxysuccinimide ester (amino acid 21) and from the dipeptide ester the N-protected group is hydrogenolytically removed, the glycyl-glutamide-tert.butyl ester (amino acids 21–22) is linked with Nα-benzyloxycarbonyl-asparaginyl-Nε-tert.butyloxycarbonyl-lysine (amino acids 19–20) in accordance with the carbodiimide-N-hydroxysuccinimide method in accordance with the literature to form benzyloxycarbonyl-tetra-peptide ester and from this the N-protective group is removed with catalytically exited hydrogen and the asparaginyl-Nε-tert.butyloxycarbonyl-lysyl-glycyl-glutamine-tert.butyl ester (amino acids 19–22) obtained is combined with Nα-benzyloxy-carbonyl-Nδ, ω-di-benzyloxycarbonyl-arginine-4-nitrophenyl ester (amino acid 18) to form Nα-benzyloxycarbonyl-Nδ,ω-di-benzyloxycarbonyl-arginyl-asparaginyl-Nε-tert-.butyloxycarbonyl-lysyl-glycyl-glutamine-tert.butyl ester, following which the three benzyloxycarbonyl protective groups are removed by catalytic hydrogenolysis with the addition of 2 equivalents of hydrogen bromide with a formation of the fragment I.

The first method subembodiment can be modified in that the Nα-benzyloxycarbonyl-asparaginyl-Nε-tert-.butyloxycarbonyl-lysine (amino acids 19 and 20) is produced by amino-acylation of Nε-tert. butyloxycarbonyl-lysine with Nα-benzyl-oxycarbonyl-asparagine-4-nitrophenyl ester in a conventional manner.

A second subembodiment of the method is characterized in that the fragment II is produced by the linking of Nα-benzyloxycarbonyl-Nε-tert.butyloxycarbonyl-lysine-N-hydroxysuccinimide ester (amino acid 16) and glutaminic acid- γ-tert.butyl-α-methyl ester (amino acid 17) and the compound obtained is converted by alkaline ester saponification and following catalytic deacylation perform Nε-tert. butyloxycarbonyl-lysyl-glutaminic acid-γ-tert.butyl ester (amino acids 16–17), following which after double stepwise built up with the use of respectively Nα-benzyloxycarbonyl-glutaminic acid (γ-tert.butyl ester) -N-hydroxysuccinimide ester (amino acids 15 and 14 respectively) as a respective head component the fragment II is formed.

A third subembodiment of the method is characterized in that the fragment III is produced in that norleucin (amino acid 13) is aminoacylated with the help of Nα-benzyloxycarbonyl Nδ,Nω-di-benzyloxycarbonyl-arginine-N-hydroxysuccinimide ester (amino acid 12).

A fourth subembodiment of the method is characterized in that the fragment IV is produced in that leucyl-glutamine (amino acids 10–11) known in the literature is linked with Nα-benzyloxycarbonyl-glutaminic acid-(γ-tert.butyl ester) -N-hydroxysuccinimide ester under synthesis conditions.

A fifth subembodiment of the method is characterized in that the fragment V is produced in that the O-tert.butyl-tyrosyl-glycine (amino acids 7–8) known in the literature is linked with Nα-benzyloxycarbonyl-O-tert.butyl-threonine-N-hydroxysuccinimide ester (amino acid 6) under synthesis conditions and the compound obtained is converted into the fragment V by catalytic splitting off of the N-protective group.

A sixth subembodiment of this method is characterized in that the fragment VI is produced by linking Nα-benzyloxycarbonyl-isoleucine (amino acid 4) and phenylalanine-tert. butyl ester (amino acid 5) in accordance with the carbodiimide method known in the literature and after catalytic deacylation of the compound formed the isoleucyl-phenylalanin-tert.butyl ester (amino acids 4–5) obtained is linked with N α-tert.butyloxycarbonyl-valyl-proline in accordance with the carbodiimide method known in the literature to form Nα-tert.butyloxycarbonyl valyl-prolyl-isoleucyl-phenylalanine-tert.butyl ester and the latter is converted by the action of trifluoro acetic acid to form valyl-prolyl-isoleucyl-phenylalanine (amino acids 2–5) to which in a conventional manner Nα-tert.butyloxycarbonylphenylalanin-N-hydroxysuccinimide ester (amino acid 1) is linked with the formation of the fragment VI.

The sixth method subembodiment can be modified in that the Nα-tert.butyloxycarbonyl-valyl-proline (amino acids 2–3) is produced in that Nα-tert.butyloxycarbonyl-valine (amino acid 2) and proline-methyl ester (amino acid 3) are combined in accordance with the phosphorazo method known in the literature to form Nα-tert.butyloxycarbonyl-valyl-proline-methyl ester and the compounds obtained is saponified under alkaline conditions or that Nα-tert.butyloxycarbonyl-valine-N-hydroxy-succinimide ester is converted with 2 equivalents of proline.

A seventh subembodiment of the method is characterized in that (a) for linking the fragments I to VI firstly fragment I is linked with fragment II in accordance with the dicyclohexylcarbodiimide-N-hydroxysuccinimide method known in the literature and the compound obtained is converted by catalytic hydrogenolysis into glutamyl (γ-tert.butyl ester)-glutamyl (γ-tert.butyl ester) Nε-tert.butyloxycarbonyl-lysyl-glutamyl (γ-tert.butyl ester)-arginyl (hydrobromide)-asparaginyl-Nε-tert.butyl-oxycarbonyl-lysyl-glycyl-glutamine-tert.butyl ester (amino acids 14–22), (b) following which there is linked to the compound obtained the fragment III in accordance with the dicyclohexylcarbodiimid-N-hydroxy-succinimide method known in the literature and from the compound obtained the three benzyloxycarbonyl protective groups are removed by the action of catalytically exited hydrogen and during the hydrogenation the guanido function coming free of the arginine is neutralized with hydrobromic acid with a formation of the hydro-bromide of arginyl (hydrobromide) norleucyl-glutamyl (γ-tert.butyl ester)-glutamyl-(γ-tert.butyl ester)- Nε-tert-.butyloxycarbonyl-lysyl-glutamyl-(γ-tert.butyl ester)-arginyl (hydrobromide)-asparaginyl-Nε-tert.butyloxycarbonyl-lysyl-glycyl-glutamine-tert.butyl ester (amino acids 12–22), (c) following which there is joined to the compound produced the fraction IV in accordance with the dicyclohexylcarbodiimid-N-hydroxy-succinimide or -hydroxybenzotriazole method known in the literature and the compound obtained is coverted by hydrogenolytic splitting off of the benzyloxycarbonyl protective group to form glutamyl (γ-tert.butyl ester)-leucyl-glutaminyl-arginyl (hydrobromide)-norleucyl-glutamyl (γ-tert. butyl ester) -glutamyl (γ-tert.butyl ester)-Nε-tert.butyloxycarbonyl-lysyl-glutamyl (γ-tert-.butyl ester)-arginyl (hydrobromide)-asparaginyl-Nε-tert.butyloxycarbonyl-lysyl-glycyl-glutamine-tert.butyl ester (amino acids 9–22) and isolated in the form of the hydrobromide and tetrahydrate, (d) following which the compound obtained is synthetically joined by the dicyclohexylcarbodiimid-N-hydroxysuccinimide method known in the literature with the reaction product from the reaction of the fragment V with the fragment VI which had previously been converted into the (N-hydroxysuccinimide) ester, and (e) finally from the compound obtained (amino acids 1–22) all protective groups are removed with the help of trifluoroacetic acid.

An eighth subembodiment of the method is characterized in that the trifluoroacetate and bromide ions formed by the splitting off of the protective groups are exchanged by column chromatography with the use of a weak basic anion exchange resin, which constitutes a product of condensation of epichlorhydrin and ammonia, possesses tertiary aliphatic amino radicals as functional groups and is present in the acetate form.

The eighth method subembodiment can be modified in that the 13 norleucine-14-desamido-motilin obtained is purified by column chromatography using a strongly basic anion exchange resin on the basis of modified dextrane with diethyl-(2-hydroxy-propyl)-aminoethyl radicals as functional groups and following this on a strongly acid cation exchange resin on the basis of modified dextrane with sulfopropyl radicals as functional groups.

The subject matter of the invention also comprises an agent with a motilin action, which is characterized by a content of 13-norleucine-14-desamido-motilin as an active component.

With the invention it is possible to make available a compound which can be produced fully synthetically and in high yields and after purification on ion exchangers has an activity of above 90% of naturally occurring motilin, something which is to be regarded as an indication that the sequence site of the methionine can also be occupied by norleucine. This finding is surprising in as far as the replacement of methionine by norleucine in naturally occurring humane gastrin I leads to a synthetic product, which only has approximately 10% gastrin activity.

Besides having the above stated utilities for known motilin, 13-norleucine-14-desamido-motilin also has the following utility: pepsin can be made by stimulating pepsin release and isolation of the pepsin released; antibodies can be produced and isolated; the pepsin level can be determined by stimulating pepsin release, taking a sample of gastric juice and measuring the pepsin content - these things being achieved by the use of 13-norleucine-14-desamido-motilin. 13-norleucine-14-desamido-motilin is a therapeutic agent and can be used in diagnosis.

The invention will now be explained in more detail by the accompanying drawings, wherein.

Figure 1:
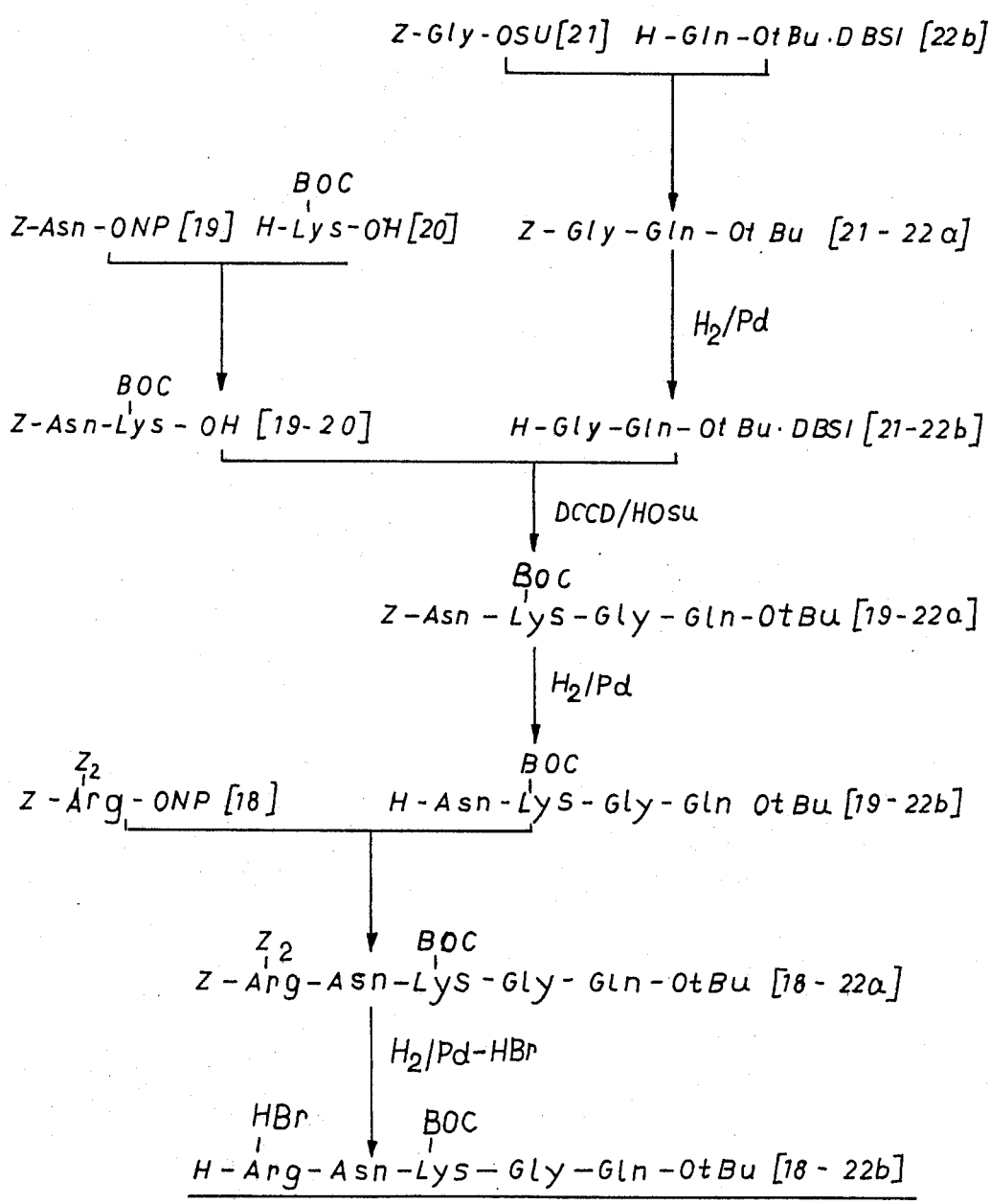
FIG. 1, shows a synthesis diagram for the production of the fragment I.
Figure 2:
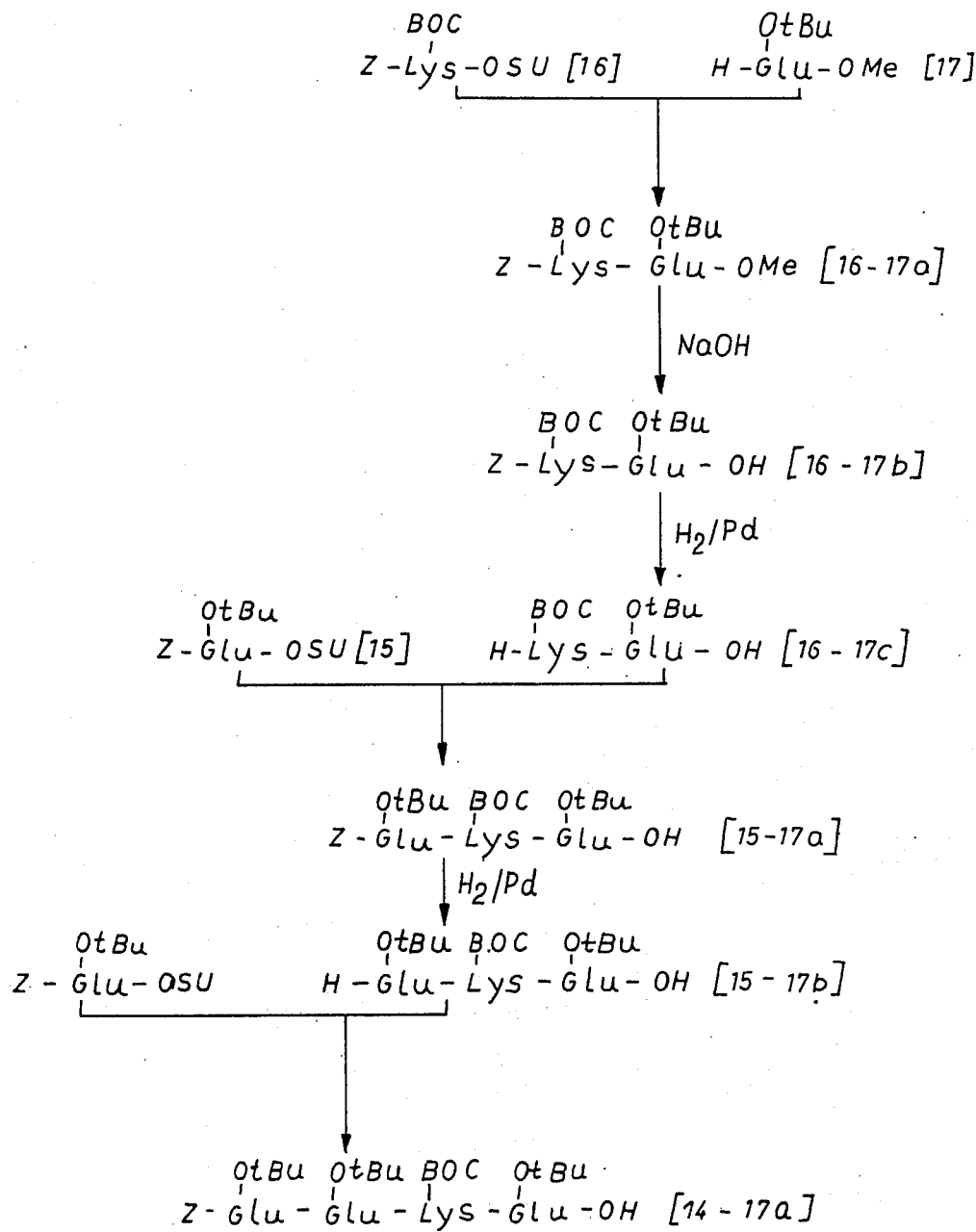
FIG. 2 shows a synthesis diagram for the production of the fragment II.
Figure 3:
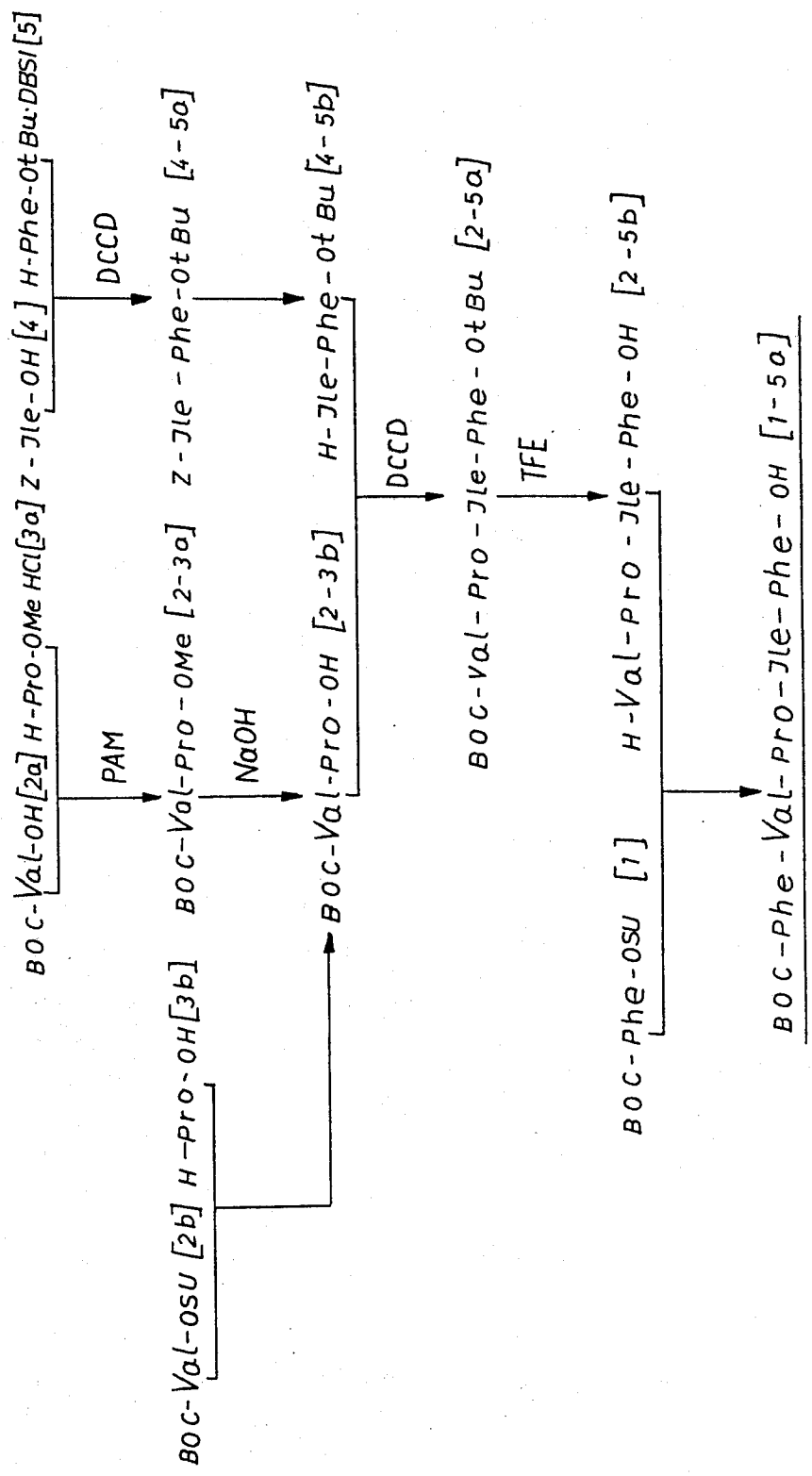
FIG. 3 shows a synthesis diagram for the production of the fragment VI.
Figure 4:
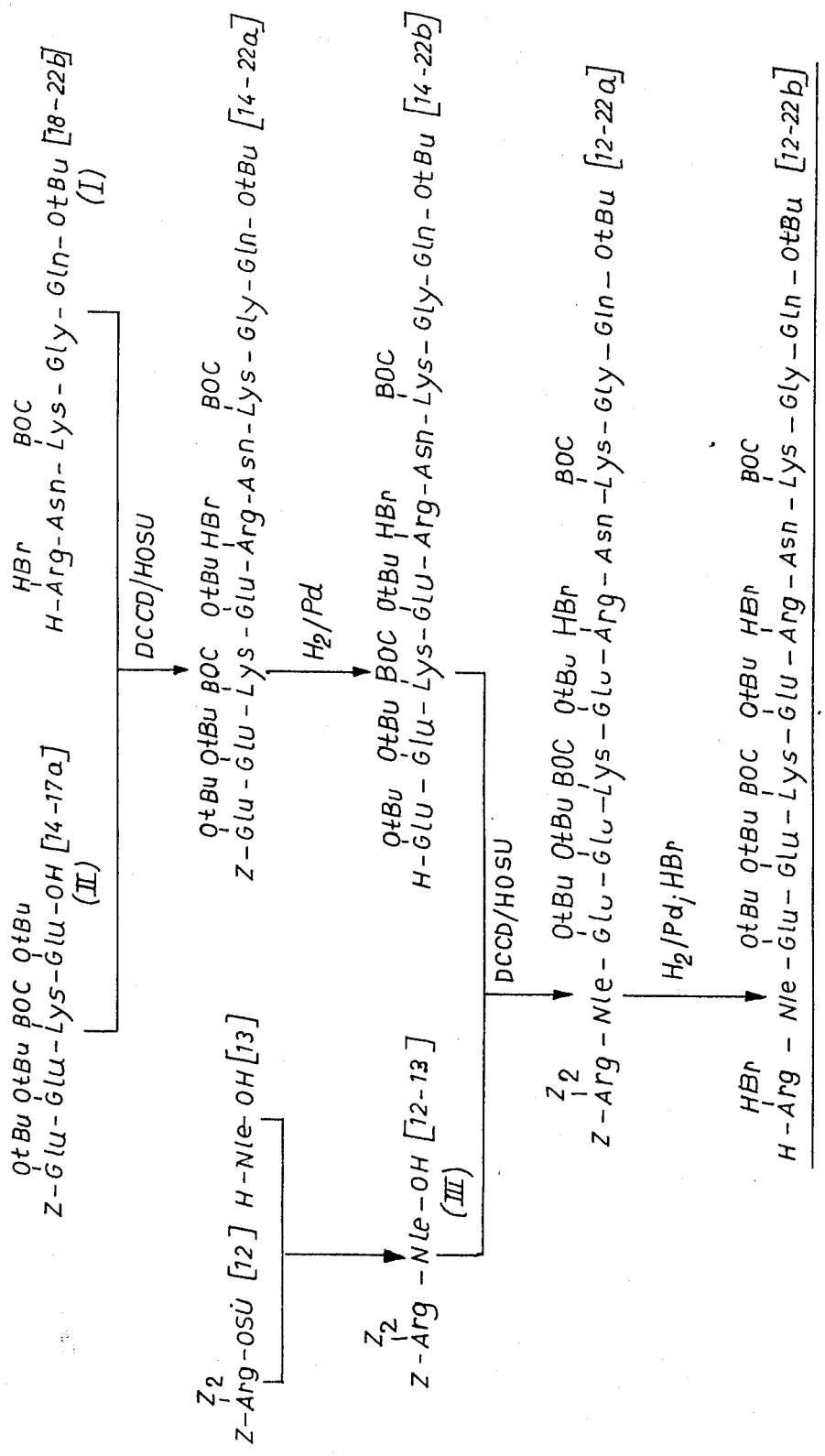
FIG. 4 shows a synthesis diagram for the production of the fragment III and for linking up the fragments I + II + III.
Figure 5:
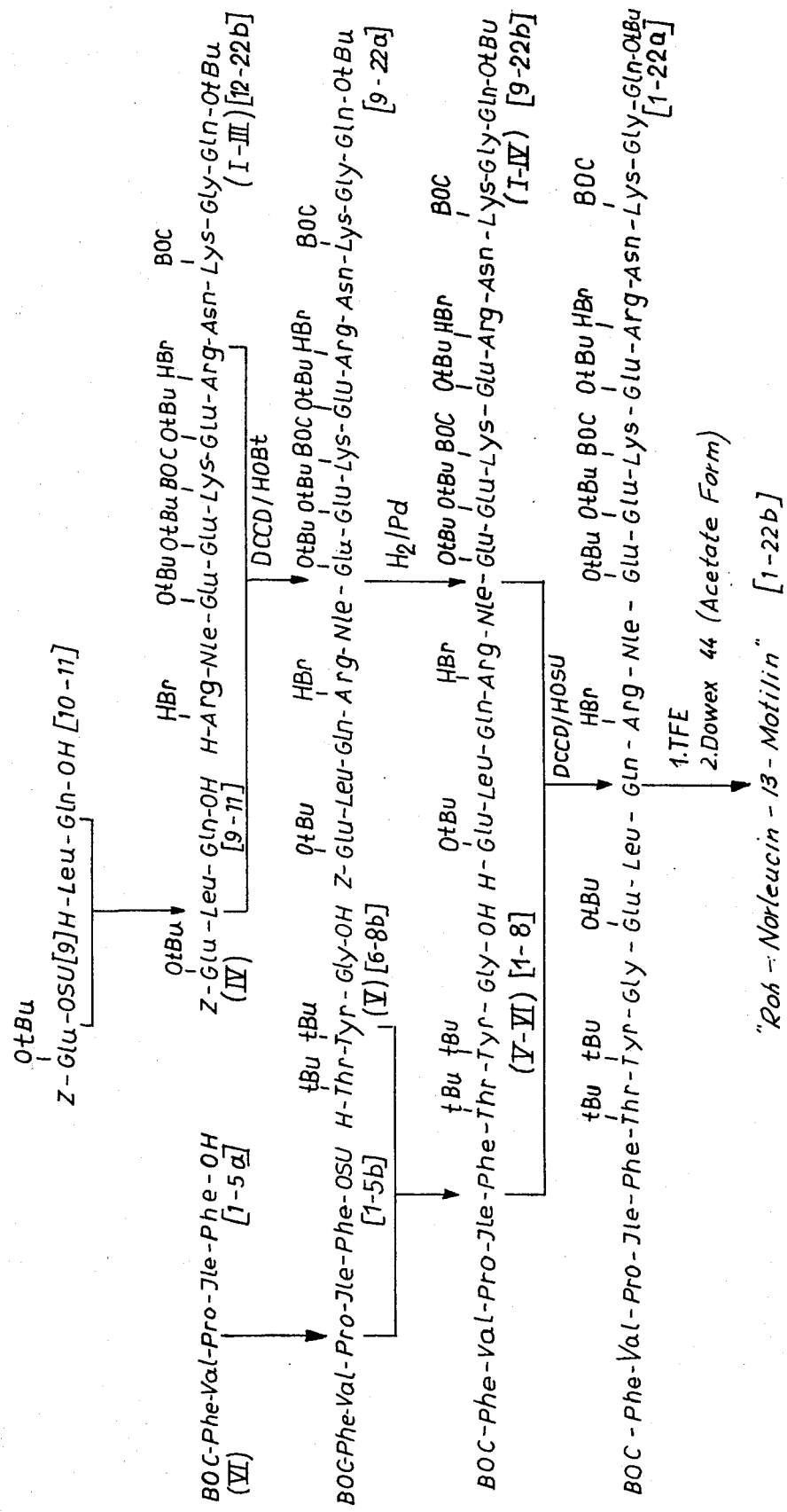
FIG. 5 shows a synthesis diagram for the production of the fragment IV and for linking up the fragments IV with (I–III), VI with V, and (I–IV) with (V–VI).

The following examples are intended to explain the invention in more detail and represent the preferred embodiments of this invention. In the figures and examples the following abbreviations and symbols conventional in peptide chemistry are employed:

Amino acid abbreviations formed of 3 letters, in the case of which it is a question generally of the 3 starting letters, numerical data in brackets, indicating the position within the polypeptide chain and not comprising any further addition, if the compound in question does not occur in the form of a further derivative, which however are serially provided with the additions a, b, c, etc., when a is taken as a starting point and further derivatives are produced, L as an indication of the configuration, Z for the benzyloxycarbonyl radical (reference should be had for example to Bergmann et al in "Berichte D. Dtsch. Chem. Ges.", vol. 65, 1932, pages 1192 et seq.), BOC for the tert.butyloxycarbonyl radical (reference should be had for example to McKay et al. in "J. Am. Chem. Soc.", vol. 79, 1957, pages 4686 et seq. and Anderson et al. in "J. Am. Chem. Soc.", vol. 79, 1957, pages 6180 et seq.), DCCD for the dicyclohexylcarbodiimide method (reference should be had for example to Sheehan et al in "J. Am. Chem. Soc.", vol. 77, 1955, pages 1067 et seq.), DCCD/HOSU for the dicyclohexylcarbodiimide-N-hydroxy-succinimide method (reference should be had for example to Wünsch et al. in "Berichte d. Dtsch. Chem. Ges.", vol. 99, 1966, pages 110 et seq. and Weygand et al. in "Zeitschr. f. Naturforschg.", vol. 216, 1966, pages 426 et seq., and also König et al. in "Berichte d. Dtsch. Chem. Ges.", vol. 103, 1970, pages 788 et seq.), DCCD/HOBt for the dicyclohexylcarbodiimide-hydroxybenzo-triazole method (reference should be had for example to Konig et al in "Ber. d. Dtsch. Chem. Ges.", vol. 103, 1970, pages 788 et seq.), PAM for the phosphorazo method (reference should be had for example to Goldschmidt in "Angew. Chem.", vol. 62, 1950, pages 538 et seq. and Goldschmidt et al. in "Liebigs Ann.", vol. 580, 1953, pages 68 et seq.), SU for the N-hydroxysuccinimide radical, NP for the p-nitrophenyl radical, tBu for the tert.butyl radical, DBSI for dibenzolsulfimide as a salt former, Me for the methyl radical, TFE for trifluoroacetic acid, i.v. for in vacuo, F for "flow point" (= melting point), and (Z) after indication of flow point for "with decomposition".

EXAMPLE 1

Production of the fragment I (part sequences18-22)

H-Gln-OtBu (22b), which can be obtained from Z-Gln-OH (22a) by esterification with tert.butyl acetate with catalysis by sulfuric acid and subsequent hydrogenolytic removal of the benzyloxycarbonyl-protective group, was linked with Z-Gly-OSU (21) to form benzyloxycarbonyl-dipeptide ester (21–22a); the H-Gly-Gln-OtBu (21–22b) obtained after hydrogenolytic removal of the N-protective group was linked with Z-Asn-Lys-(BOC)-OH (19–20) in accordance with the carbodiimide-N-hydroxysuccinimide method described by Wünsch and Weygand in the above-mentioned literature reference or in accordance with the modification of this method described by Geiger in the literature reference cited to form benzyloxy-carbonyltetrapeptide-tertbutyl ester (19–22a). The head component (19–20) could be obtained by aminoacylation of H-Lys-(BOC)-OH 20) with Z-Asn-ONP (19) under conventional conditions.

Removal of the benzyloxycarbonyl-protective group from Z-Asn-Lys-(BOC)-Gly-Gln-OtBu (19–22a) by means of catalytically excited hydrogen led to the tetrapeptide ester derivative (19–22b), which was joined with Z-Arg-(δ,ω-Z$_2$)-ONP (18) to Z-Arg-(δ,ω-Z$_2$)-Asn-Lys-(BOC)-Gly-Gln-OtBu (18–22a).

The experimental preparation was as follows:

A. L-glutamine-tert.butyl ester dibenzenesulfimide salt 103 g benzyloxycarbonyl-glutamine-tert.butyl ester, obtained in accordance with the method described by Schnabel et al. in "Liebigs Ann.", vol. 686, 1965, pages 229 et seq. in 2 l methanol were hydrogenated catalytically (palladium black) in a conventional manner with the addition drop by drop of 91 g dibenzenesulfimide in 500 ml methanol at pH 3.5

The filtrate was evaporated in vacuo (i.v.), the operation being terminated with azeotropic distillation with benzene; on mixing with diethylether crystallisation occurred in the ethyl acetate solution of the oily residue. From methanol/diethylether crystals were produced with F = 135° – 136°; $[\alpha]_D^{20} = +10.78°$ (c = 1.0; in methanol). Yield = 146 g (97 % of the theoretical amount).

B. Benzyloxycarbonyl-glycyl-L-glutamine-tert.butyl ester 115 g L-glutamine-tert.butyl ester dibenzenesulfimide salt suspended in 800 ml dichloromethane were mixed with 32.2 ml triethylamine and following this were mixed with 70.5 g benzyloxycarbonyl-glycine-N-hydroxysuccinimide ester while stirring. Stirring at room temperature, evaporation i.v., taking up the oil in ethyl acetate, washing of this solution in a conventional manner with citric acid, potassium hydrogen carbonate solution and water, drying over sodium sulfate and evaporation i.v. led to an oil. Yield = 87 g (93 % of the theoretical amount).

C. Glycyl-L-glutamine-tert.butyl ester dibenzenesulfimide salt 80 g benzyloxycarbonyl-glycyl-L-glutamine-tert.butyl ester (in accordance with B) in 900 ml methanol were deacylated hydrogenolytically as described in (A) above (60 g dibenzenesulfimide) and processed. The product was an oily residue, which on digesting in petroleum ether crystallised; F = 92° (Z); $[\alpha]_D^{20} = -8.5°$ (c = 1.0; in methanol). Yield = 110 g (98 % of the theoretical amount).

D. Benzyloxycarbonyl-L-asparaginyl-Nε-tert.butyloxycarbonyl-L-lysine 51 g Nε-tert.butyloxycarbonyl-L-lysine were converted in a conventional manner into the benzyltriethylammonium salt and then stirred in 700 ml dimethylformamide with 81 g benzyloxycarbonyl-L-asparagine-4-nitrophenyl ester with the addition of 1 equivalent of pyridine for 48 hours at 20°. The residue left after vacuum evaporation was treated with ethyl acetate and potassium hydrogen sulfate solutions simultaneously; the thick precipitate formed was filtered off and then recrystallised from ethanol/petroleum ether. F = 174° – 175° (Z); $[\alpha]_D^{20} = +13.8°$ (c = 1.0; in pyridine). Yield = 70 g (71 % of the theoretical amount).

E. Benzyloxycarbonyl-L-asparaginyl-Nε-tert.butyloxycarbonyl-L-lysyl-glycyl-L-glutamine-tert.butyl ester 61.5 g glycyl-L-glutamine-tert.butyl ester dibenzenesulfimide salt and 54.5 g benzyloxycarbonyl-L-asparaginyl-Nε-tert.butyloxycarbonyl-L-lysine in 700 ml dimethylformamide were mixed while stirring at 0°C firstly with 15.5 ml triethylamine and after 15 minutes with 13 g N-hydroxysuccinimide and also 23 g N,N'-dicyclohexylcarbodiimide. After 3 hours stirring was continued again for a further 24 hours at room temperature. The filtrate from N,N'-dicyclohexylurea was evaporated i.v.; the residue crystallised on treatment with ethyl acetate. Recrystallisation was carried out from methanol/water and isopropanol/ethyl acetate. F = 155° – 156°; $[\alpha]_d^{20} = -20.8°$ (c = 1.0; in ethanol). Yield = 63 g (78 % of the theoretical amount).

F. L-asparaginyl-Nε-tert.butyloxycarbonyl-L-lysyl-glycyl-L-glutamine-tert.butyl ester hydrochloride 47.5 g benzyloxycarbonyl-L-asparaginyl-Nε-tert.butyloxycarbonyl-L-lysyl-glycyl-L-glutamine-tert.butyl ester (in accordance with E) were conventionally hydrogenated in 800 ml methanol under pH stat-conditions (pH = 5.5; 25.2 ml 2.5 N-hydrogen chloride solution in methanol). The filtrate after evaporation i.v. yielded an oil; a colourless powder was obtained after digestion in diethyl ether. F = 98°; $[\alpha]_D^{20} = +9.5°$ (c = 1.0 methanol). Yield = 40 g (97 % of the theoretical amount).

G. Nα.Nδ.Nω-tris-benzyloxycarbonyl-L-arginyl-L-asparaginyl-Nε-tert.butyloxycarbonyl-L-lysyl-glycyl-L-glutamine-tert.butyl ester 31.9 g L-asparaginyl-Nε-tert.butyloxycarbonyl-L-lysyl-glycyl-L-glutamine-tert.butyl ester hydrochloride (in accordance with F) and 33.68 g Nα.Nδ.Nω-tris-benzyloxycarbonyl-L-arginine-N-hydroxysuccinimide ester in 1 l dimethylformamide were mixed at 0°C with 7 ml triethylamine; after 24 hours of stirring at room temperature, evaporation i.v., reprecipitation from methanol/water and following this recrystallisation from methanol resulted in a colourless powder; $[\alpha]_D^{20} = -7.6°$ (c = 1.0; in glacial acetic acid). Yield = 46.5 g (80 % of the theoretical amount).

H. L-arginyl (hydrobromide)-L-asparaginyl-Nε-tert.butyloxycarbonyl-L-lysyl-glycyl-L-glutamine-tert.butyl ester hydrobromide dihydrate 45.5 g Nα.Nδ.Nω-tris-benzyloxycarbonyl-L-arginyl-L-asparaginyl-Nε-tert.butyloxycarbonyl-L-lysyl-glycyl-L-glutamine-tert.butyl ester (in accordance with G) in 1.5 l dimethylformamide/methanol (2:1) were deacylated hydrogenolytically under pH-stat conditions in a conventional manner (pH = 4.5; 80 ml 1 N-hydrobromic acid). Evaporation of the filtrate i.v. and reprecipitation of the residue from ethanol/diethyl ether led to an amorphous powder; $[\alpha]_D^{20} = -4.8°$ (c = 1.0; in 80 % acetic acid). Yield = 37 g (98 % of the theoretical amount).

Yield 55 % taking all stages on the basis of H-Gln-OtBu (22b) as a starting material; $[\alpha]_D^{20} = -7.6 \pm 1°$ or $[\alpha]_{546}^{20} = -9.4°$ (c = 1 in acetic acid); chromatographically pure in 3:1:1 n-butanol/glacial acetic acid/water and 5:1:1 n-heptane/tert.butanol/glacial acetic acid;

analysis calculated/found: C 57.98/57.70; H 6.69/6.56; N 13.29/13.29; / 22.02/22.45.

By catalytic removal of the three benzyloxy-carbonyl masks by catalytic hydrogenolysis with the addition of two equivalents of hydrogen bromide the desired fraction I was obtained, that is to say H-Arg-(HBr)-Asn-Lys-(BOC)-Gly-Gln-OtBu.HBr (18–22b).

Yield 98 %; $[\alpha]_D^{20} = -4.8 \pm 1°$ or $[\alpha]_{546}^{20} = -6.05°$ (c = 1 in 80 % acetic acid); chromatographically pure in 3:1:1 n-butanol/glacial acetic acid/water and 35:35:30 tert.amylalcohol/pyridine/water;

analysis calculated/found: C 40.21/40.46; H 6.85/6.93; N 16.12/15.89; Br 16.72/16.51.

EXAMPLE 2

Production of the fragment II (part sequences 14–17)

As expected Z-Lys (BOC)-OSU (16) and H-Glu (OtBu)-OMe (17) can satisfactorily be combined to form benzyloxycarbonyl-dipeptide ester (16–17a); alkaline ester saponification and following catalytic deacylation led via the dipeptide derivative (16–17b) to H-Lys (BOC)-Glu (OtBu)-OH (16–17c). In a double step-by-step build-up method with the help of Z-Glu-(OtBu)-OSU (15 and 14, respectively) as the respective head component finally the fragment II, that is to say Z-Glu-(OtBu)-Glu (OtBu)-Lys (BOC)-Glu (OtBu)-OH (14–17a) was obtained.

The experimental preparation was carried out in a manner similar to that described in example 1.

Yield 48 % taking all stages into account on the basis of the H-Glu (OtBu)-OMe (17); F 3 147°–149°; $[\alpha]_D^{20} = -9.8 \pm 1°$ or $[\alpha]_{546}^{20} = -12.3°$ (c = 1 in dimethylformamide) chromatographically pure in 45:45:10 cyclohexane/chloroform/glacial acetic acid;

analysis calculated/found: C 59.02/58.70; H 7.86/8.04; N 7.48/7.72.

EXAMPLE 3

Production of the fragment III (part sequences 12–13)

The production of the fragment III, that is to say Z-Arg ($\delta,\omega$-$Z_2$)-Nle-OH (12–13) was successfully carried out with the yield of 86 % by aminoacylation of norleucine (13) using Z-Arg ($\delta,\omega$-$Z_2$)-OSU (12).

The experimental preparation was carried out in a manner similar to that described in example 1. F = 130–132°; $[\alpha]_D^{20} = +7.2 \pm 1°$ and, respectively, $[\alpha]_{546}^{20} = +8.4°$ (c = 1 in glacial acetic acid); chromatographically pure in 5:1:1 n-heptane/tert.butanol/glacial acetic acid and 3:1:1 n-butanol/glacial acetic acid/water;

analysis calculated/found: C 62.69/62.45; H 6.28/6.28; N 10.15/10.16.

EXAMPLE 4

Production of the fragment IV (part sequences 9–11)

The dipeptide H-Leu-Gln-OH synthetised in accordance with the method described in "Berichte d. Dtsch. Chem. Ges.", vol. 104, 1971, pages 2430 et seq., was used as the part of the sequence (10–11). Linking of Z-Glu (OtBu)-OSU (9) to the dipeptide (10–11) led to the fragment IV with a yield of 74 %, that is to say Z-Glu (OtBu)-Leu-Gln-OH (9–11).

The experimental preparation was carried out in a manner similar to that described in example 1. F = 146–148°; $[\alpha]_D^{20} = -31.6 \pm 1°$ and, respectively, $[\alpha]_{546}^{20} = -38.1°$; (c = 1 in methanol); chromatographically pure in 5:1:1 n-heptane/tert.butanol/glacial acetic acid and 3:1:1 n-butanol/glacial acetic acid/water;

analysis calculated/found: C 58.12/58.05; H 7.32/7.24; N 9.68/9.48.

EXAMPLE 5

Production of the fragment V (part sequences 6–8)

The dipeptide H-Tyr (tBu)-Gly-OH synthetised in accordance with the method described in "Zeitschr. f. Physiol. Chem.", vol. 353, 1972, pages 1246 et seq., was used as the part of the sequence (7–8). Linking of H-Tyr (tBu)-Gly-OH (7–8) with Z-Thr (tBu)-OSU (6) led to the benzyloxycarbonyltripeptide (6–8a), which by using catalytic dibenzyloxycarbonylation resulted in the desired fragment V, that is to say H-Thr (tBu)-Tyr (tBu)-Gly-OH (6–8b).

The experimental preparation was carried out in a manner similar to that described in example 1. Yield: approximately 81 % for both stages on the basis of the dipeptide used (7–8); F = 126°–127°; $[\alpha]_D^{20} = +7.9 \pm 1°$ and, respectively, $[\alpha]_{546}^{20} = +8.9°$ (c = 1 in methanol); chromatographically pure in 35:35:30 tert.amyl alcohol/pyridine/water;

analysis calculated/found: C 60.88/60.69; H 8.30/8.31; N 8.88/8.91 related to a dipeptide with 1/4 mole glacial acetic acid of crystallisation.

EXAMPLE 6

Production of the fragment VI (part sequences 1–5)

In accordance with the carbodiimide method indicated Z-Ile-OH (4) was linked with H-Phe-OtBu (5). By means of subsequent catalytic diacylation of the intermediate benzyloxy-carbonyl-dipeptide ester (4–5a) it was possible to isolate H-Ile-Phe-OtBu (4–5b) with a yield of above 90 %.

Simultaneously BOC-Val-OH (2a) and H-Pro-OMe (3a) were united in accordance with the indicated phosphorazo method to form tert.butyloxycarbonyl-dipeptide ester (2–3a); subsequent alkaline ester saponification led to BOC-Val-Pro-OH (2–3b) with a yield of above 70 %. The production of (2–3b) by reaction of BOC-Val-OSU (2b) with two equivalents of proline (3b) was simpler and led to a higher yield (83 %).

Both dipeptide derivatives could be united with the help of the carbodiimide method indicated to form BOC-Val-Pro-Ile-Phe-OtBu (2–5a); the action of trifluoroacetic acid on (2–5a) led to the free tetrapeptide H-Val-Pro-Ile-Phe-OH (2–5b) which was built up in a conventional manner with BOC-Phe-OSU (1) to form BOC-Phe-Val-Pro-Ile-Phe-OH (1–5a) (fragment VI).

The experimental preparation was carried out in a manner similar to that described in example 1. Yield: 63 % over the last three stages on the basis of (4–5b); F = 218°; $[\alpha]_D^{20} = 64.2 \pm 1°$ and, respectively, $[\alpha]_{546}^{20} = -75.82°$ (c = 1 in acetic acid); chromatographically pure in 3:1:1 n-butanol/glacial acetic acid/water and 35:35:30 tert.amyl alcohol/pyridine/water;

analysis calculated/found: C 64.88/64.72; H 7.64/7.70; N 9.70/9.61.

EXAMPLE 7

Condensation of the fragments I to VI (overall sequences 1–22)

With the help of the dicyclohexylcarbodiimide-N-hydroxy-succinimide method cited the fragment II (14–17a) could be very satisfactorily linked with the carboxyl terminal fragment I (18–22b); the N-benzyloxycarbonyl-nonapeptide-tert.-butyl ester (14–22a) could be converted satisfactorily by catalytic hydrogenolysis into H-Glu (OtBu)-Glu (OtBu)-Lys-(BOC)-Glu (OtBu)-Arg (HBr)-Asn-Lys (BOC)-Gly-Gln-OtBu (14–22b). The linking of the fragment III with the above nonapeptide ester derivative (14–22b) was again carried out with the help of the above-mentioned method in a satisfactory manner with the formation of Z-Arg (δ,ω-Z₂)-Nle-Glu (OtBu)-Glu (OtBu)-Lys-(BOC)-Glu (OtBu)-Arg (HBr)-Asn-Lys (BOC)-Gly-Gln-OtBu (12–22a), which could be isolated with the desired degree of purity.

The yield was about 69 % for all three stages, on the basis of the fragment I used; $[\alpha]_D^{20} = -4.9 \pm 1°$ and, respectively, $[\alpha]_{546}^{20} = -6.9°$ (c = 0.7 in methanol); chromatographically pure in 3:1:1 n-butanol/glacial acetic acid/water and 3:2:1 n-heptane/tert.butanol/glacial acetic acid;

analysis calculated/found: C 55.48/55.24; H 7.29/7.27 N 12.82/12.62; O 20.92/20.97; Br 3.48/3.20.

The action of catalytically excited hydrogen on the undeca-peptide derivative (12–22a) led to removal of the three benzyloxycarbonyl protective groups; after neutralisation of the guanido function so released with hydrobromic acid (undertaken during the hydrogenation) H-Arg (HBr)-Nle-Glu-(OtBu)-Glu-Gln-OtBu (OtBu)-Lys (BOC)-Glu (OtBu)-Arg (HBr)-Ash-Lys-(BOC)-Gly-Gln-OtBu (12–22b) in the form of the hydrobromide was obtained.

Condensation of the fragment IV (9–11) onto the undeca-peptide-tert.butyl ester (12–22b) was carried out successfully in accordance with the dicyclohexylacarbodiimide-N-hydroxybenzo-triazole method cited.

From the product of joining, the tetra-decapeptide derivative (9–22a) after hydrogenolytic splitting off of the benzyloxycarbonyl protective group it was possible to obtain H-Glu (OtBu)-Leu-Gln-Arg (HBr)-Nle-Glu (OtBu)-Glu-(OtBu)-Lys (BOC)-Glu (OtBu)-Arg (HBr)-Asn-Lys (BOC)-Gly-Gln-OtBu (9–22b), again in the form of the hydrobromide and as a tetrahydrate in a pure state.

Yield for both stages 77 %. $[\alpha]_D^{20} = -6.3 \pm 1°$ and, respectively, $[\alpha]_{546}^{20} = -8.3°$ (c = 0.7 in methanol); chromatographically pure in 3:1:1 n-butanol/glacial acetic acid/water;

analysis calculated/found: C 47.99/47.81; H 7.58/7.28; N 13.72/13.69; amino acid analysis: Lys 1.99;Arg 1.98;Asp 1.03;Glu 6.30; Gly 0.98;Leu 0.97;Nle 1.01.

During the course of the above-described condensation of parts the fragments V (6–8a) and VI (1–5a) were combined after their conversion into the (N-hydroxysuccinimide) ester (1–5b); it was however not possible to obtain this part, that is to say BOC-Phe-Val-Pro-Ile-Phe-Thr (tBU)-Tyr (tBu)-Gly-OH (1–8) in a pure condition. Having regard to the amino acid analysis data the octapeptide derivative was contaminated with approximately 10 % (1–5a or b); attempts to divide up the mixture did not lead to success. The "raw" part obtained (1–8) from the fragments V and VI was again linked with the tetradecapeptide derivative (9–22b) from the fractions (I–IV) again in accordance with the dicyclohexylcarbodiimide-N-hydroxysuccinimide method cited to give BOC-Phe-Val-Pro-Ile-Phe-Thr (tBu)-Tyr (tBu)-Gly-Glu (OtBu)-Leu-Gln-Arg (HBR)-Nle-Glu (OtBu)-Glu (OtBu)-Lys (BOC)-Glu (OtBu)-Arg (HBr)-Asn-Lys-(BOC)-Gly-Gln-OtBu (1–22a); after splitting off of all protective groups by using anhydrous trifluoroacetic acid and following exchange of the trifluoroacetate and bromide ions by ion exchange chromatography on a conventional weakly basic ion exchange resin having the trade name "Dowex 44", made up of epichlorohydrin with ammonia and having tertiary aliphatic amino groups (acetate form) a "raw 13 norleucine-14-desamido-motilin" (1–22b) was obtained, which having regard to the use of "impure" part (1–8) must have been impaired by a "spurious sequence".

The experimental conduct of the fragment condensation was as follows:

A. Condensation I with II 9.2 g of fragment I (in accordance with example 1 H), 9.36 g of benzyloxycarbonyl-L-glutamyl (γ-tert.butyl ester)-L-glutamyl (γ-tert.butyl ester)-Nε-tert.butyloxycarbonyl-L-lysyl-L-glutamic acid-γ-tert.butyl ester (fragment II) and 1.4 ml triethylamine in 200 ml dimethylformamide were mixed at 0°C with 2.3 g of N-hydroxysuccinimide and then with 3.1 g of N,N′-dicyclohexylcarbodiimide; the reaction mixture was stirred at 5°C for 24 hours and at room temperature for 4 days and the filtrate was evaporated i.v. The residue was digested several times with water and finally precipitated twice from methanol/ethyl acetate.

The resulting product was benzyloxycarbonyl-L-glutamyl-(γ-tert.butyl ester)-L-glutamyl-(γ-tert.butyl ester)-Nε-tert.butyloxycarbonyl-L-lysyl-L-glutamyl-(γ-tert.butyl ester)-L-arginyl-(hydrobromide)-L-asparaginyl-Nε-tert.butyloxycarbonyl-L-lysyl-glycyl-glutamine-tert.butyl ester in the form of an amorphous powder. $[\alpha]_D^{20} = -14.6°$(c = 1.0; in dimethylformamide) Yield = 14.8 g (84 % of theoretical amount).

12.3 g of the compound obtained in 800 ml of methanol were catalytically hydrogenated under pH-stat conditions in a conventional manner (pH = 5.5; 7 ml 1 N-hydrobromic acid). The filtrate was evaporated i.v. and the residue was twice precipitation from ethanol/ethyl acetate.

The resulting product was L-glutamyl (γ-tert.butyl ester)-L-glutamyl (γ-tert.butyl ester)-Nε-tert.butyloxycarbonyl-L-lysyl-L-glutamyl (ε-tert.butyl ester)-L-arginyl (hydrobromide)-L-asparaginyl-Nε-tert.butyloxycarbonyl-L-lysyl-glycyl-glutamine-tert.butyl ester hydrobromide as the desired product of condensation. $[\alpha]_D^{20} = -21.5°$ (c = 1.0; in methanol) Yield = 11.4 g (96 % of the theoretical amount).

B. Condensation (I-II) with III 3.4 g of nonapeptide-tert.butyl ester (in accordance with A) and 2.8 g of Nα.Nδ.Nω-tris-benzyloxycarbonyl-L-arginyl-L-norleucine (fragment III) in 200 ml of dimethylformamide and 0.70 g of N-hydroxysuccinimide were mixed at −10°C with 0.28 ml of triethylamine and following this with 0.825 g of N,N′-dicyclohexylcarbodiimide. The mixture was stirred for 24 hours at +4°C and 24 hours at room temperature. After the removal of the dimethylformamide i.v. the residue was reprecipitated from methanol/ethyl acetate, then digested with water and again precipitated from methanol/ethyl acetate.

The resulting product was Nα.Nδ.Nω-tris-benzyloxycarbonyl-L-arginyl-L-norleucyl-L-glutamyl (γ-tert.butyl ester)-L-glutamyl (γ-tert.butyl ester)-Nε-tert.butyloxycarbonyl-L-lysyl-L-glutamyl (γ-tert.butyl ester)-L-arginyl (hydrobromide)-L-asparaginyl-Nε-L-asparaginyl-Nε-tert.butyloxycarbonyl-L-lysyl-glycyl-glutamine-tert.butyl ester in the form of an amorphous powder. $[\alpha]_D^{20} = -4.9°$ (c = 0.7; in methanol) Yield = 3.9 g (85 % of theoretical amount).

3.5 g of the undecapeptide derivative obtained in 800 ml of methanol were catalytically hydrogenated under pH-stat conditions in a conventional manner (pH approximately 4.5; 31 ml 0.1 N-hydrogen bromide solution in methanol). The residue from the filtrate evaporated i.v. was reprecipitated from methanol/ethyl acetate.

The resulting product was L-arginyl (hydrobromide)-L-norleucyl-L-glutamyl (γ-tert.butyl ester)-L-glutamyl (γ-tert.butyl ester)-Nε-tert.butyloxycarbonyl-L-lysyl-L-glutamyl-(γ-tert.butyl ester)-L-arginyl (hydrobromide)-L-asparaginyl-Nε-tert.butyloxycarbonyl-L-lysyl-glycyl-glutamine-tert.butyl ester-hydrobromide in the form of a powder. $[\alpha]_D^{20} = -21.7°$ (c = 1.0; in methanol) Yield = 3.0 g (95 % of the theoretical amount).

C. Condensation (I–II–III) with IV 2.7 g of undecapeptide-tert.butyl ester-hydrobromide (in accordance with B), 1.5 g of benzyloxycarbonyl-L-glutamyl-(γ-tert.butyl ester)-L-leucyl-L-glutamine (fragment IV) and 0.405 g of 1-hydroxybenzotriazole in 200 ml of dimethylformamide were mixed at 0°C with 0.182 ml of triethylamine and following this with 0.577 g of N,N′-dicyclohexylcarbodiimide. The reaction mixture was stirred for 24 hours at between 0° and +5°C and then for a further period of 5 days at 25°C. The vacuum evaporation residue was twice reprecipitated from methanol/ethyl acetate, and after drying i.v. was digested with water and then again precipitated from methanol/diethylether. The resulting product was benzyloxycarbonyl-L-glutamyl-(γ-tert.butyl ester)-L-leucyl-L-glutaminyl-L-arginyl(hydrobromide)-L-norleucyl-L-glutamyl(γ-tert.butyl ester)-L-glutamyl-(γ-tert.butyl ester)-Nε-tert.butyloxycarbonyl-L-lysyl-L-glutamyl (γ-tert.butyl ester)-L-arginyl (hydrobromide-L-asparaginyl-Nε-tert.butyloxycarbonyl-L-lysyl-glycyl-L-glutamine-tert. butyl ester dihydrate in the form of an amorphous powder. $[\alpha]_D^{20} = -4.3°$ (c = 0.7; in methanol) Yield = 2.7 g (82 % of the theoretical amount).

2.0 g of the tetradecapeptide derivative obtained in 800 ml of methanol were hydrogenated under pH-stat conditions in a conventional manner catalytically (pH about 4.5; 8 ml of 0.1 N-hydrobromic acid). The evaporated filtrate left a residue, which has reprecipitated from menthanol/ethyl acetate.

The resulting product was L-glutamyl (γ-tert.butyl ester)-L-leucyl-L-glutaminyl-L-arginyl (hydrobromide)-L-norleucyl-L-glutamyl (γ-tert.butyl ester)-L-glutamyl (γ-tert.butyl ester)-Nε-tert.butyloxycarbonyl-L-lysyl-L-glutamyl (γ-tert.butyl ester)-L-arginyl (hydrobromide)-L-asparaginyl-Nε-tert.butyloxycarbonyl-L-lysyl-glycyl-L-glutamine-tert.butyl ester hydrobromide-tetrahydrate in the form of an amorphous powder. $[\alpha]_D^{20} = -6.3°$ (c = 0.7; in methanol) Yield = 1.92 g (94% of the theoretical amount).

D. Condensation V with VI 21.6 g of the fragment VI and 6.9 g of N-hydroxysuccinimide in 400 ml of dimethylformamide were mixed at −5°C with 6.3 g of N,N′-dicyclohexylcarbodiimide and the reaction mixture was stirred for 2 hours at 0°C and then stirred overnight at room temperature. The filtrate was evaporated i.v.; the oily residue was crystallised from isopropanol.

The resulting product was tert.butyloxycarbonyl-L-phenylalanyl-L-valyl-L-prolyl-L-isoleucyl-L-phenylalanine-N-hydroxysuccinimide ester. F = 190°–192°; $[\alpha]_D^{20} = +59.28°$ (c = 1.0; in dioxan) Yield 21.3 g (88 % of the theoretical amount).

12.2 g of fragment V and 3.8 ml of triethylamine in 400 ml of dimethylformamide were mixed with 14.8 g of the tert.butyloxycarbonylpentapeptide-N-hydroxysuccinimide ester mentioned; the reaction mixture was evaporated after 24 hours of stirring at room temperature i.v. and the resulting oily residue was distributed between ethyl acetate and citric acid solution. The ethyl acetate phase was conventionally washed, dried, and evaporated to dryness i.v. Minute colourless crystals were obtained from ethyl acetate/petroleum ether, which consisted of tert.butyloxycarbonyl-L-phenylalanyl-L-valyl-L-propyl-L-isoleucyl-L-phenylalanyl-O-tert.butyl-L-threonyl-O-tert.butyl-L-tyrosyl-glycine. $[\alpha]_D^{20} = −44.0°$ (c = 1.0; in ethanol) Yield = 18.2 g (87 % of the theoretical amount).

E. Condensation (I-II-III-IV) with (V-VI)

1.3 g of tetradecapeptide-tert.butyl ester hydrobromide (in accordance with C) and 1.17 g of tert.butyloxycarbonyloctapeptide (in accordance with D), 0.07 ml of triethylamine and 0.175 g of N-hydroxysuccinimide (in further tests 0.20 g of hydroxybenzotriazole was used) in 100 ml of dimethylformamide were mixed at −10°C with 0.257 g of N,N′-dicyclohexylcarbodiimide. The mixture was stirred for 2 days at 0°C and 3 days at room temperature. After removal of the solvent i.v. the residue was carefully digested with hot acetic ester. The resin-like product was reprecipitated from methanol/ethyl acetate and after digestion with ethyl acetate was dried and following this was treated for 5 hours exhaustively with water.

After reprecipitation from methanol/water an amorphous powder (1.1 g) was obtained consisting of tert.butyloxycarbonyl-L-phenylalanyl-L-valyl-L-prolyl-L-isoleucyl-L-phenylalanyl-O-tert.butyl-L-threonyl-O-tert.butyl-L-tyrosylglycyl-L-glutamyl (γ-tert.butyl ester)-L-leucyl-L-glutaminyl-L-arginyl (hydrobromide)-L-norleucyl-L-glutamyl (γ-tert.butyl ester)-L-glutamyl (γ-tert.butyl ester)-Nε-tert.butyloxycarbonyl-L-lysyl-L-glutamyl (γ-tert.butyl ester)-L-arginyl (hydrobromide)-L-asparaginyl-Nε-tert.butyloxycarbonyl-L-lysyl-glycyl-L-glutamine-tert.butyl ester.

0.2 g of the protected product obtained had 20 ml of ice-cold trifluoro acetic acid poured on it and the mixture was left standing for 2 hours at room temperature. Following this the excess trifluoro acetic acid was removed i.v. at the lowest possible temperature. The remaining material was taken up in diluted acetic acid. The solution obtained was twice treated with 4 g of a weakly basic anion exchanger in the OH-form, following which the exchanger eluate was lyophilised. Yield = 157 mg.

EXAMPLE 8

Pure preparation of the synthetic product

A. In accordance with the purification, carried out in a highly successful manner, of natural motilin ion exchange chromatography was carried out of 25 mg of the raw-norleucine-13-motilin obtained on a strongly basic anion exchanger resin, present in the acetate-form and known under the trade name of "QAE-Sephadex A-25" on the basis of a modified dextran with diethyl-(2-hydroxypropyl)-aminoethyl radicals as functional groups.

The experimental conditions were as follows:

column: 30 × 0.9 cm; 25 mg of the raw product dissolved in 2 ml of 0.5 % ammonia;
eluting agent: 0.025 M-ammonium acetate solution (adjusted with diluted ammonia to pH 9.27);
flow speed: 18 ml/hour; 6 ml-fractions.

Figure 6:
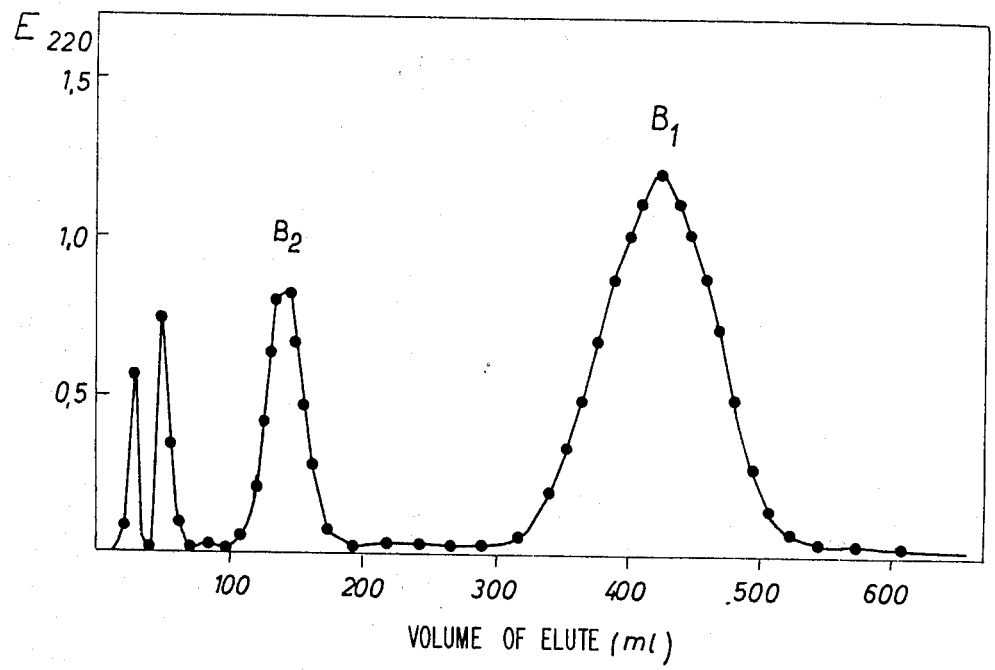
FIG. 6 shows the column chromatographic elution curve of raw 13 norleucine-14-desamido-motilin on a strongly basic anion exchanger.

There resulted a division up into two principal fractions, as is shown by Fig. 6.

The fraction $B_2$ (approximately 4 mg) was found to be the expected spurious sequence (1–5/9–22) while the fraction $B_1$ (approximately 12 mg) was the norleucine-13-motilin sought. The docosapeptide obtained by freeze drying in a solid condition was found to be chromatographically uniform in a system 30:6:24:20 n-butanol/glacial acetic acid/water/pyridine and 30:12:24:20 n-butanol/glacial acetic acid/water/pyridine and also in accordance with paper and thin layer chromatography.

An amino acid analysis of the fractions $B_1$ and $B_2$ was carried out after acidic hydrolysis (6N-HC1, 20 hours), in the course of which it was found that in the case of a hydrolysis time of 72 hours practically the same values were obtained. The results obtained are listed in the following table I.

Table I

| | Fraction | | Calculated ratio for |
| | $B_1$ | $B_2$ | $(Nle^{13})$-motilin |
|---|---|---|---|
| Lys | 1.98 | 2.04 | 2 |
| Arg | 1.98 | 1.99 | 2 |
| Asp | 1.00 | 1.01 | 1 |
| Thr | 1.00 | — | 1 |
| Glu | 6.08 | 6.00 | 6 |
| Pro | 0.97 | 0.91 | 1 |
| Gly | 1.99 | 1.06 | 2 |
| Val | 0.94 | 0.88 | 1 |
| Ile | 0.95 | 0.86 | 1 |
| Leu | 1.00 | 0.99 | 1 |
| Nle | 1.01 | 1.00 | 1 |
| Tyr | 0.91 | — | 1 |
| Phe | 1.82 | 1.73 | 2 |

Tests for purposes of orientation showed that there was a biological activity of the freeze dried $B_1$-fraction of at least 50 %.

Enzymatic degradation tests substantially confirmed the proposed primary structure.

B. The manner of procedure given in (A) was repeated using the following experimental conditions:
column: 80 × 1.5 cm;
235 mg of raw product, dissolved in 15 ml of 0.5 % ammonia were introduced into the column which had been equilibriated with 0.025 M-ammonium acetate solution (adjusted with diluted ammonia to pH 9.20);
eluting agent: 0.025 M-ammonium acetate solution (pH 9.20); speed of flow: 47 ml/hour;
23.5 ml-fractions collected, peptide distribution determined by measuring the extinction at 220 nm.

A division up into the $B_1$-fraction (135 mg) and $B_2$-fraction (44 mg) was obtained, the weight data being expressed in terms of the lyophilised fractions.

C. For further purification 135 mg of the $B_1$-fraction were treated on a strongly acidic cation exchanger resin present in the ammonium form and known under the trade name "SP-Sephadex C-25", on the basis of a modified dextran with sulfopropyl radicals as functional groups, for column chromatography. The experimental conditions were as follows:
column: 80 × 1.5 cm;
135 mg of $B_1$-fraction, dissolved in 10 ml of 0.5 % acetic acid;

eluting agent: (1) 0.025 M-ammonium acetate solution (produced using 0.025 M-acetic acid, adjusted by the addition of diluted ammonia to pH 5.0); 24 hours at a flow speed of 110 ml/hour; (2) 0.025 M-ammonium acetate solution (pH 5.38);
flow speed: 110 ml/hour;
37 ml-fractions.

Figure 7:
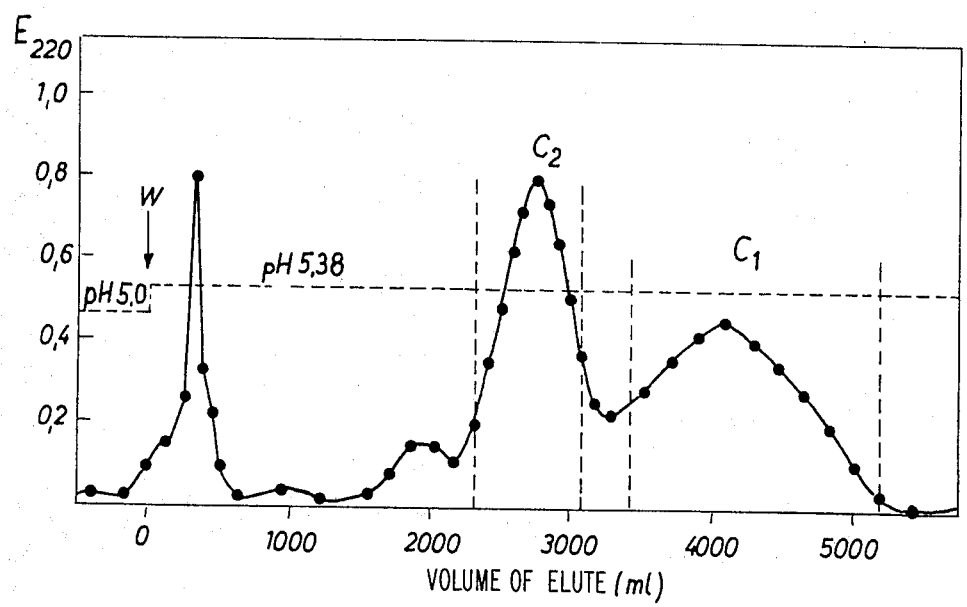
FIG. 7 shows the column chromatographic elution curve of the fraction $B_1$ of FIG. 6 on a strongly acid cation exchanger.

FIG. 7 indicates the part of the elution curve obtained after changing the eluting agent. As is apparent two principal fractions, that is to say $C_1$ (57 mg) and $C_2$ (48 mg) were obtained.

The $C_2$-fraction was biologically inactive while the $C_1$-fraction had a biological activity of over 90 % in comparison with natural motilin (reference is directed to J. C. Brown et al., "Can. J. Physiol. Pharmacol.", vol. 49, 1971, pages 399 to 405, and "Gastroenterology", vol. 62, 1972, pages 401 to 404).

The results of the amino acid analyses are given in the following table II.

Table II

| | $C_1$ | $C_2$ |
|---|---|---|
| Lys | 1.99 | 1.98 |
| Arg | 2.03 | 1.96 |
| Asp | 1.00 | 1.03 |
| Thr | 1.00 | 1.00 |
| Glu | 6.08 | 6.14 |
| Pro | 0.99 | 1.05 |
| Gly | 2.02 | 2.03 |
| Val | 0.95 | 0.91 |
| Ile | 0.95 | 0.90 |
| Leu | 1.00 | 1.00 |
| Nle | 0.99 | 1.00 |
| Tyr | 0.91 | 0.91 |
| Phe | 1.92 | 1.91 |

What we claim is:
1. A method for the production of 13-norleucine-14-desamido-motilin comprising:
a. forming fragment I, which consists of arginyl (hydrobromide)-asparagine-Nε-tert.butyloxycarbonyl-lysyl-glycyl-glutamine-tert.butyl ester (amino acids 18 to 22), by esterifying Nα-benzyloxycarbonyl-glutamine with acetic acid tert.butyl ester using a sulfuric acid catalysis, hydrogenolytic removing the N-protective group to form glutamine tert.butyl ester (amino acid 22), reacting the glutamine tert-.butyl ester with Nα-benzyloxycarbonyl-glycine-N-hydroxy-succinimide ester (amino acid 21) and hydrogenolytically removing the N-protected group from the dipeptide ester, reacting the glycyl-glutamine-tert.butyl ester (amino acids 21 to 22) with Nα-benzyloxycarbonyl-asparaginyl-Nε-tert-.butyloxycarbonyl-lysine (amino acids 19 to 20) by means of the carbodiimide-N-hydroxysuccinimide method to form benzyloxy-carbonyl-tetra-peptide ester, removing the N-protective group from the benzyloxy-carbonyl-tetra-peptide ester by means of catalytic hydrogenation, reacting the resultant asparaginyl-Nε-tert.butyloxycarbonyl-lysyl-glycyl-glutamine-tert.butyl ester (amino acids 19 to 22) with Nα-benzyloxycarbonyl-Nδ,ω-dibenzyloxycarbonyl-arginine-4-nitrophenyl ester (amino acid 18) to form Nα-benzyloxycarbonyl-Nδ,ω-di-benzyloxycarbonyl-arginyl-asparaginyl-Nε-tert.butyloxycarbonyl-lysyl-glycyl-glutamine-tert.butyl ester, and removing the three benzylocarbonyl protective groups from the resultant ester by means of catalytic hydrogenolysis with the addition of 2 equiva- lents of hydrogen bromide whereby fragment I is formed;

b. forming fragment II, which consists of Nα-benzyloxycarbonyl-glutamyl- (γ-tert.butyl ester)-glutamyl-(γ-tert.butyl ester)-Nε-tert.butyloxycarbonyl-lysyl-glutamic acid-γ-tert.butyl ester (amino acids 14 to 17), by reacting Nα-benzyloxycarbonyl-Nε-tert.butyloxy-carbonyl-lysine-N-hydroxysuccinimide ester (amino acid 16) and glutaminic acid -γ-tert.butyl-α-methyl ester (amino acid 17), converting the resultant compound by alkaline ester saponification and subsequent catalytic deacylating to Nε-tert.butyloxycarbonyl-lysyl-glutamic acid-γ-tert.butyl ester (amino acids 16 and 17), and twice, sequentially, reacting said ester with Nα-benzyloxycarbonyl-glutamic acid (γ-tert.butyl ester)-N-hydroxysuccinimide ester (amino acids 15 and 14, respectively), such respectively being a head component;

c. forming fragment III which consists of Nα-benzyloxy-carbonyl-Nδ, Nω-di-benzyloxycarbonyl-arginyl-norleucine (amino acids 12 and 13), by aminoacylating norleucin (amino acid 13) with Nα-benzyloxycarbonyl Nδ, Nω-dibenzyloxy-carbonyl-arginine-N-hydroxysuccinimide ester (amino acid 12);

d. forming fragment IV which consists of Nα-benzylocarbonyl-glutamyl-(γ-tert.butyl ester)-leucyl-glutamine (amino acids 9 to 11), by reacting leucyl-glutamine (amino acids 10 and 11) with Nα-benzyloxy-carbonyl-glutaminic acid-(γ-tert.butyl ester) N-hydroxysuccinimide ester;

e. forming fragment V which consists of 0-tert.butyl-threonyl-0-tert.butyl-tyrosyl-glycine (amino acids 6 to 8), by reacting 0-tert.-butyl-tyrosyl-glycine (amino acids 7 and 8) with Nα-benzyloxycarbonyl-0-tert.-butyl-threonine-N-hydroxysuccinimide ester (amino acid 6) and converting the compound into fragment V by catalytic hydrogenation of the N-protective group;

f. forming fragment VI which consists of Nα-tert.butyloxy-carbonyl-phenylalanyl-valyl-prolyl-isoleucyl-phenylalanine (amino acids 1 to 5), by reacting Nα-benzyloxy-carbonyl-isoleucine (amino acid 4) and phenylalanine-tert.-butyl ester (amino acid 5) using the carbodiimide method, catalytic deacylating of the resultant compound, reacting the resultant isoleucyl-phenylalanin-tert.-butyl ester (amino acids 4 and 5) with Nα-tert.-butyloxycarbonyl-valyl-proline using the carbodiimide method, whereby Nα-tert.butyloxycarbonyl valyl-prolyl-isoleucyl-phenylalanine-tert.-butyl ester is formed, converting the resultant ester by treatment with trifluoro acetic acid to valyl-prolyl-isoleucyl-phenylalanine (amino acids 2 to 5), and reacting the amino function with Nα-tert.butyl-oxycarbonyl-phenylalanin-N-hydroxysuccinimide ester (amino acid 1), whereby fragment VI is formed, wherein, in fragments I to VI, all of the side chain functions of the polyfunctional amino acids have tert.butyl alcohol derived protective groups, which can acidolytically readily be removed, and the complex function of the arginine is masked either by Nδ, ω-diacylation or by protonisation by salt formation with hydrogen bromide, said fragments I to VI being separately formed, in any desired sequence or concurrently;

g. connecting fragments I to VI together by means of the N,N'-dicyclohexylcarbodiimide-N-hydroxysuccinimide method or a modification thereof;

h. removing all of the protective groups from the so-obtained polypeptide, masked on all sides and having the overall sequence of the amino acids 1 to 22, by means of tri-fluoro-acetic acid;

i. removing the trifluoroacetate and bromide ions by means of an anion exchange resin; and j. isolating and purifying the resultant 13-norleucine-14-desamido-motilin.

2. A method according to claim 1 wherein the Nα-benzyloxycarbonyl-asparaginyl-Nε-tert-butyloxycarbonyl-lysine (amino acids 19 and 20) is produced by aminoacylation of Nε-tert.butyloxycarbonyl-lysine with Nα-benzyloxycarbonyl-asparagine-4-nitrophenyl ester.

3. A method according to claim 1 wherein the Nα-tert.butyloxycarbonyl-valyl-proline (amino acids 2 and 3) is produced by reacting Nα-tert.butyloxycarbonyl-valine (amino acid 2) and proline-methyl ester (amino acid 3) using the phosphorazo method whereby Nα-tert.butyloxycarbonyl-valyl-proline-methyl ester forms, and saponifying the resultant compound under alkaline conditions.

4. A method according to claim 1 wherein the Nα-tert.butyloxycarbonyl-valyl proline (amino acids 2 and 3) is produced by reacting Nα-tert.butyloxycarbonyl-valine-N-hydroxy-succinimide ester with 2 equivalents of proline.

5. A method according to claim 1 wherein fragments I to VI are connected by reacting fragment I with fragment II using the dicyclohexylcarbodiimide-N-hydroxysuccinimide method, converting the resultant compound by catalytic hydrogenolysis into glutamyl (γ-tert.-butyl ester)-glutamyl (γ-tert.-butyl ester)-Nε-tert.butyloxycarbonyl-lysyl-glutamyl (γ-tert.butyl ester)-arginyl (hydrobromide)-asparaginyl-Nε-tert.butyl-oxycarbonyl-lysyl-glycyl-glutamine-tert.-butyl ester (amino acids 14 to 22), reacting the resultant compound with fragment III using the dicyclohexylcarbodiimid-N-hydroxydesuccinimide method, removing the three benzyloxycarbonyl protective groups from the resultant component by the action of catalytic hydrogenation, during the catalytic hydrogenation the liberated guanido function of the arginine being neutralized with hydrobromic acid, whereby the hydrobromide of arginyl (hydrobromide)-norleucyl-glutamyl (γ-tert.butyl ester)-glutamyl-(γtert.butyl ester)-Nε-tert.butyloxycarbonyl-lysyl-glutamyl-(γ-tert.butyl ester)-arginyl (hydrobromide)-asparaginyl-Nε-tert.butyloxy-carbonyl-lysyl-glycyl-glutamine-tert.butyl ester (amino acids 12 to 22) forms, reacting the resultant compound with fraction IV using the dicyclohexylcarbodiimide-N-hydroxysuccinimide or -hydroxybenzotriazole method, converting the resultant compound by hydrogenolytic removing the benzyloxycarbonyl protective group to form glutamyl (γ-tert.butyl ester)-leucyl-glutaminyl-arginyl (hydrobromide)-norleucyl-glutamyl (γ-tert.butyl ester)-glutamyl (γ-tert.butyl ester)-Nε-tert.butyloxycarbonyl-lysyl-glutamyl (γ-tert.butyl ester)-arginyl (hydrobromide)-asparaginyl-Nε-tert.butyloxycarbonyl-lysyl-glycyl-glutamine-tert-butyl ester (amino acids 9 to 22), isolating the resultant compound in the form of the hydrobromide and tetrahydrate, reacting the resultant compound by the dicyclohexylcarbodiimide-N-hydroxysuccinimide method with the reaction product for fragment V with fragment VI, which had been converted into the (N-hydroxysuccinimide) ester, and removing all protective groups from the resultant compound (amino acids 1 to 22) trifluoroacetic acid.

6. A method according to claim 1 wherein the trifluoroacetate and bromide ions formed by the removal of the protective groups are exchanged by column chromatography using a weakly basic anion exchange resin, which is a product of condensation of epichlorhydrin and ammonia, possesses tertiary aliphatic amino residues as functional groups and is present in the acetate form.

7. A method according to claim 6 wherein the resultant 13-norleucine-14-desamindo-motilin is purified by column chromatography suing a strongly basic anion exchange resin, which is a modified dextrane having diethyl-(2-hydroxy-propyl)-amino-ethyl residues as functional groups, and followed by using a strongly acid cation exchange resin, which is a modified dextrane having sulfopropyl radicals as functional groups.

* * * * *